US00PP21812P2

(12) United States Plant Patent
Seto

(10) Patent No.: US PP21,812 P2
(45) Date of Patent: Mar. 22, 2011

(54) ***GENTIANA* PLANT NAMED 'HEIDELOVE3GO'**

(50) Latin Name: ***Gentiana triflora*×*Gentiana scabra***
Varietal Denomination: Heidelove3go

(75) Inventor: Takaho Seto, Tatsuno-machi (JP)

(73) Assignee: Sky Blue Seto Inc., Nagano (JP)

( * ) Notice: Subject to any disclaimer, the term of this patent is extended or adjusted under 35 U.S.C. 154(b) by 0 days.

(21) Appl. No.: 12/658,737

(22) Filed: Feb. 12, 2010

(51) Int. Cl.
*A01H 5/00* (2006.01)

(52) U.S. Cl. ..... Plt./433
(58) Field of Classification Search ..... Plt./433

See application file for complete search history.

*Primary Examiner*—Kent L Bell
(74) *Attorney, Agent, or Firm*—C. A. Whealy

(57) ABSTRACT

A new and distinct cultivar of *Gentiana* plant named 'Heidelove3go', characterized by its upright plant habit; vigorous growth habit; strong and sturdy flowering stems; freely branching habit; freely flowering habit; and large purple-colored flowers.

1 Drawing Sheet

Botanical designation: *Gentiana triflora*×*Gentiana scabra.*

Cultivar denomination: 'HEIDELOVE3GO'.

BACKGROUND OF THE INVENTION

The present invention relates to a new and distinct cultivar of *Gentiana* plant, botanically known as *Gentiana triflora*× *Gentiana scabra*, typically grown as a cut flower, and hereinafter referred to by the name 'Heidelove3go'.

The new *Gentiana* plant is a product of a planned breeding program conducted by the Inventor in Nagano, Japan. The objective of the breeding program is to create new *Gentiana* plants with large and attractive flowers.

The new *Gentiana* plant originated from a cross-pollination made by the Inventor in September, 2002, of an unnamed selection of *Gentiana triflora* var. *japonica*, not patented, as the female, or seed, parent with an unnamed selection of *Gentiana scabra*, not patented, as the male, or pollen, parent. The new *Gentiana* plant was discovered and selected by the Inventor as a single flowering plant from within the progeny of the stated cross-pollination grown in a controlled greenhouse environment in Nagano, Japan in September, 2004.

Asexual reproduction of the new *Gentiana* plant by tissue culture in Nagano, Japan, since February, 2005, has shown that the unique features of this new *Gentiana* plant are stable and reproduced true to type in successive generations.

SUMMARY OF THE INVENTION

Plants of the new *Gentiana* have not been observed under all possible environmental conditions. The phenotype may vary somewhat with variations in environment such as temperature and light intensity without, however, any variance in genotype.

The following traits have been repeatedly observed and are determined to be the unique characteristics of 'Heidelove3go'. These characteristics in combination distinguish 'Heidelove3go' as a new and distinct cultivar of *Gentiana:*

1. Upright plant habit.
2. Vigorous growth habit.

3. Strong and sturdy flowering stems.
4. Freely branching habit.
5. Freely flowering habit.
6. Large purple-colored flowers.

Plants of the new *Gentiana* differ from plants of the female parent selection in the following characteristics:

1. Plants of the new *Gentiana* have longer flowering stems than plants of the female parent selection.
2. Plants of the new *Gentiana* flower more uniformly than plants of the female parent selection.
3. Flowers of plants of the new *Gentiana* open more fully than flowers of plants of the female parent selection.
4. Plants of the new *Gentiana* and the female parent selection differ in flower color as plants of the female parent selection have pink-colored flowers.

Plants of the new *Gentiana* differ from plants of the male parent selection in the following characteristics:

1. Plants of the new *Gentiana* have longer flowering stems than plants of the male parent selection.
2. Plants of the new *Gentiana* flower earlier and more uniformly than plants of the male parent selection.
3. Flowers of plants of the new *Gentiana* have longer corollas than flowers of plants of the male parent selection.
4. Plants of the new *Gentiana* and the male parent selection differ in flower color as plants of the male parent selection have pink-colored flowers.

Plants of the new *Gentiana* can be compared to plants of the *Gentiana* 'Yumehaiji2go', not patented. In side-by-side comparisons conducted in Nagano, Japan, plants of the new *Gentiana* differed from plants of 'Yumehaiji2go' in the following characteristics:

1. Plants of the new *Gentiana* had longer, broader and stronger flowering stems than plants of 'Yumehaiji2go'.
2. Plants of the new *Gentiana* were more vigorous than plants of 'Yumehaiji2go'.
3. Plants of the new *Gentiana* flowered later than plants of 'Yumehaiji2go'.
4. Plants of the new *Gentiana* had larger flowers and flower clusters than plants of 'Yumehaiji2go'.

5. Plants of the new *Gentiana* and 'Yumehaiji2go' differed in flower color as plants of 'Yumehaiji2go' had light purple violet-colored flowers.
6. Flowers of plants of the new *Gentiana* were longer lasting than flowers of plants of 'Yumehaiji2go'.

Plants of the new *Gentiana* can also be compared to plants of the *Gentiana* 'Yumehaiji3go', not patented. In side-by-side comparisons conducted in Nagano, Japan, plants of the new *Gentiana* differed from plants of 'Yumehaiji3go' in the following characteristics:

1. Plants of the new *Gentiana* were more freely flowering than plants of 'Yumehaiji3go'.
2. Plants of the new *Gentiana* had larger flowers of plants of 'Yumehaiji3go'.
3. Plants of the new *Gentiana* and 'Yumehaiji3go' differed in flower color as plants of 'Yumehaiji3go' had light purple violet-colored flowers.

BRIEF DESCRIPTION OF THE PHOTOGRAPHS

The accompanying colored photographs illustrate the overall appearance of the new *Gentiana*, showing the colors as true as it is reasonably possible to obtain in colored reproductions of this type. Colors in the photographs may differ slightly from the color values cited in the detailed botanical description which accurately describe the actual colors of the new *Gentiana* plant.

The photograph at the top of the sheet comprises a side perspective view of typical flowering plants of 'Heidelove3go' grown in ground beds.

The photograph in the center of the sheet is a close-up view of typical developing flowers of 'Heidelove3go'.

The photograph at the bottom of the sheet is a close-up view of the outer and inner surfaces of a typical developed flower of 'Heidelove3go'.

DETAILED BOTANICAL DESCRIPTION

Plants used for the aforementioned photographs and following description were grown under conditions which closely approximate commercial production conditions during the summer in an outdoor nursery in Nagano, Japan. During the production of the plants, day temperatures ranged from 15° C. to 25° C. and night temperatures ranged from 10° C. to 15° C. Plants were three years old when the photographs and description were taken. In the following description, color references are made to The Royal Horticultural Society Colour Chart, 2001 Edition, except where general terms of ordinary dictionary significance are used.

Botanical classification: *Gentiana triflora*×*Gentiana scabra* 'Heidelove3go'.

Parentage:

*Female parent.*—Unnamed selection of *Gentiana triflora* var. *japonica*, not patented.

*Male parent.*—Unnamed selection of *Gentiana scabra*, not patented.

Propagation:

*Type.*—By tissue culture.

*Time to initiate roots.*—About one week at soil temperatures of 15° C. to 20° C.

*Time to produce a rooted young plant, winter.*—About six months at soil temperatures ranging from 10° C. to 15° C.

*Root description.*—Medium in thickness, fibrous; white to brown in color.

*Rooting habit.*—Moderate branching; moderately dense.

Plant description:

*Plant and growth habit.*—Perennial cut flower plant; upright plant habit; strong and sturdy flowering stems; freely branching habit; about five to eight flowering stems develop per plant; vigorous growth habit; campanulate flowers arranged in terminal and axillary clusters.

*Plant height.*—About 120 cm to 140 cm.

*Plant diameter or spread.*—About 30 cm to 40 cm.

*Flowering stem description.*—Diameter: About 1.2 mm to 2.1 mm. Internode length: About 4.5 cm to 6 cm. Strength: Strong. Texture: Smooth, glabrous. Color: Close to 147C.

Foliage description:

*Arrangement.*—Opposite, simple; sessile.

*Length.*—About 7.5 cm to 10.5 cm.

*Width.*—About 2.3 cm to 3.2 cm.

*Shape.*—Broadly lanceolate.

*Apex.*—Acute.

*Base.*—Attenuate.

*Margin.*—Entire.

*Texture, upper and lower surfaces.*—Smooth, glabrous.

*Venation pattern.*—Pinnate, reticulate.

*Color.*—Developing leaves, upper surface: Close to 143B. Developing leaves, lower surface: Close to 143C. Fully expanded leaves, upper surface: Close to 143A; venation, close to 139D. Fully expanded leaves, lower surface: Close to 143C; venation, close to 139C.

Flower description:

*Flower arrangement, shape and habit.*—Double campanulate flowers arranged in terminal and axillary clusters; flowers face mostly upright; freely flowering habit, about 25 to 38 flowers develop per plant.

*Natural flowering season.*—Plants begin flowering mid to late September in Nagano, Japan; flowers open when temperatures are above 20° C. and close when temperatures are below 20° C.

*Flower longevity as a cut flower.*—About 15 days; flowers persistent.

*Fragrance.*—None detected.

*Flower clusters.*—Quantity of flowers per cluster: Typically two to four. Height: About 5 cm to 6 cm. Diameter: About 5 cm to 6 cm.

*Flower buds.*—Length: About 5 mm. Diameter: About 4 mm. Shape: Deltoid. Color: Close to 138D.

*Flower diameter.*—About 1.9 cm to 2.1 cm.

*Flower depth (height).*—About 5.2 cm to 5.4 cm.

*Petals.*—Arrangement: About five or six in a single whorl; fused. Length: About 5.2 cm to 5.4 cm. Width: About 1.1 cm to 1.9 cm. Shape: Ovate. Apex: Acute. Margin: Entire. Texture, upper and lower surfaces: Smooth, glabrous. Color: When opening and fully opened, upper surface: Close to 78B; towards the base, close to 155D with red purple-colored streaks, close to 71A; color becoming closer to N80C with development. When opening and fully opened, lower surface: Close to 78A.

*Petaloids.*—Arrangement: About five or six in a single whorl; fused. Length: About 1.1 cm to 1.3 cm. Width: About 1.2 cm to 1.3 cm. Shape: Deltoid. Apex: Acute. Margin: Entire. Texture, upper and lower surfaces: Smooth, glabrous. Color: When opening, upper and lower surfaces: Close to N78B; towards the base, close to 155D with red purple-colored streaks, close to 71A. Fully opened, upper and lower surfaces: Close to N78A.

*Sepals.*—Arrangement: About five to six in a single whorl; fused. Length: About 1.4 cm to 1.8 cm. Width: About 2 mm to 3.5 mm. Shape: Narrowly lanceolate. Apex: Acute. Margin: Entire. Texture, upper and lower surfaces: Smooth, glabrous. Color: Developing, upper surface: Close to 138C. Developing, lower surface: Close to 138D. Fully developed, upper and lower surfaces: Close to 138D.

*Peduncles.*—Length: About 5 cm to 14 cm. Diameter: About 1.2 mm to 2.1 mm. Strength: Strong. Texture: Smooth, glabrous. Color: Close to 147C.

*Reproductive organs.*—Stamens: Quantity per flower: Five. Anther shape: Spatulate. Anther length: About 5.1 mm to 5.8 mm. Anther color: Close to 158C. Pollen amount: Scarce. Pollen color: Close to 8A. Pistils: Quantity per flower: One. Pistil length: About 3.5 cm to 3.7 cm. Stigma shape: Two-parted. Stigma color: Close to 150D. Style length: About 1.5 cm to 1.6 cm. Style color: Close to 149D.

*Seed/fruit.*—Seed and fruit production have not been observed.

Disease/pest resistance: Plants of the new *Gentiana* have not been noted to be resistant to pathogens and pests common to *Gentiana.*

Garden performance: Plants of the new *Gentiana* have exhibited good tolerance to rain, wind and temperatures ranging from about −5° C. to about 30° C.

It is claimed:

1. A new and distinct *Gentiana* plant named 'Heidelove3go' as illustrated and described.

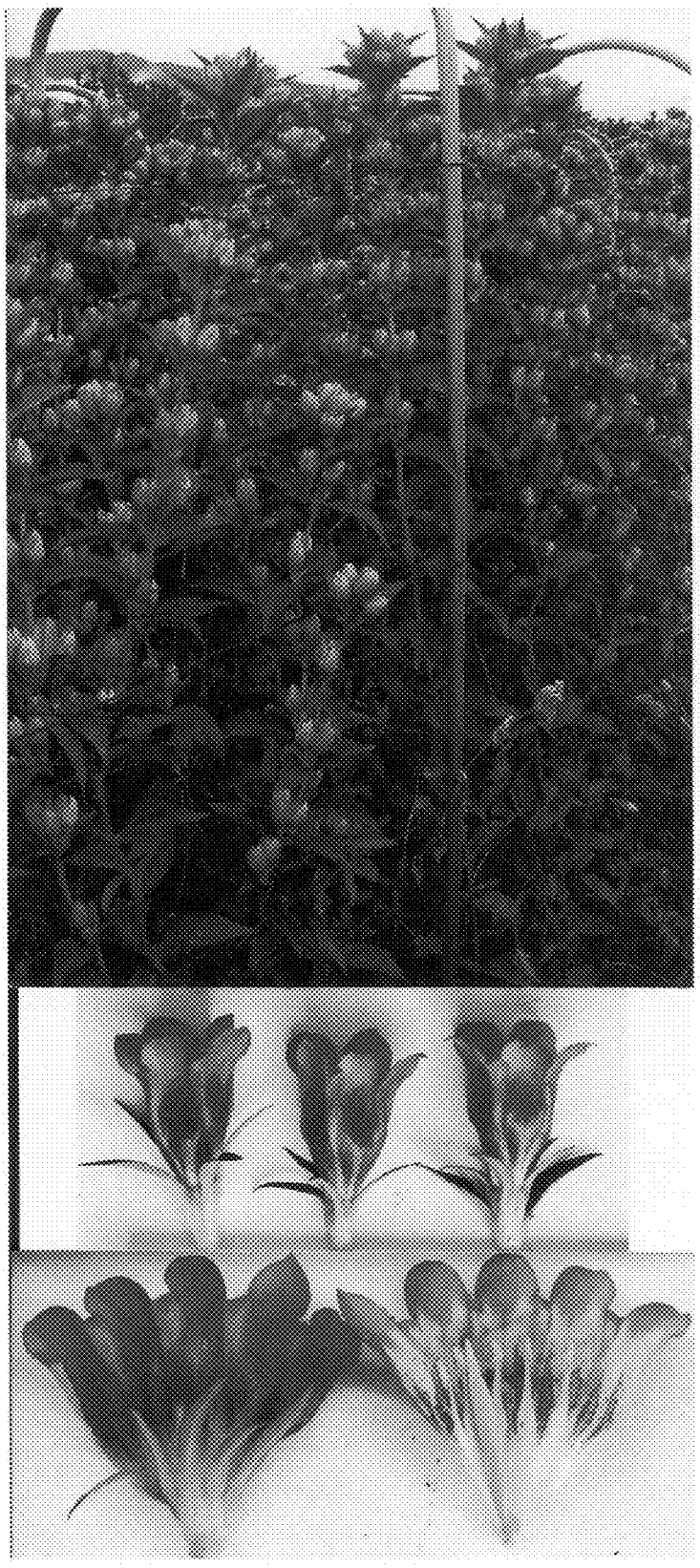

* * * * *